United States Patent
Gallem et al.

(10) Patent No.: US 6,983,747 B2
(45) Date of Patent: Jan. 10, 2006

(54) AEROSOL GENERATOR

(75) Inventors: Thomas Gallem, Munich (DE); Markus Urich, Munich (DE)

(73) Assignee: Pari GmbH Spezialisten für Effektive Inhalation, Starnberg (DE)

(*) Notice: Subject to any disclaimer, the term of this patent is extended or adjusted under 35 U.S.C. 154(b) by 42 days.

(21) Appl. No.: 10/466,929

(22) PCT Filed: Jan. 23, 2002

(86) PCT No.: PCT/EP02/00648

§ 371 (c)(1),
(2), (4) Date: Dec. 16, 2003

(87) PCT Pub. No.: WO02/064265

PCT Pub. Date: Aug. 22, 2002

(65) Prior Publication Data

US 2004/0089295 A1    May 13, 2004

(30) Foreign Application Priority Data

Jan. 23, 2001 (DE) ................................ 101 02 846

(51) Int. Cl.
*A61M 15/00* (2006.01)
*A61M 16/00* (2006.01)

(52) U.S. Cl. .................... 128/203.12; 128/200.14; 128/200.16; 128/200.21; 128/203.24; 128/204.14; 239/102.2; 239/338; 239/581.1; 239/581.2; 239/538; 239/539

(58) Field of Classification Search ........... 128/203.24, 128/200.16, 200.14, 200.21, 204.14; 239/102.2, 239/338, 581.1, 581.2, 538, 539
See application file for complete search history.

(56) References Cited

U.S. PATENT DOCUMENTS

| | | | | |
|---|---|---|---|---|
| 5,239,993 A | * | 8/1993 | Evans .................... | 128/203.15 |
| 5,429,122 A | * | 7/1995 | Zanen et al. ........... | 128/203.15 |
| 5,653,227 A | * | 8/1997 | Barnes et al. .......... | 128/203.12 |
| 5,669,378 A | * | 9/1997 | Pera et al. ............. | 128/203.21 |
| 5,765,552 A | * | 6/1998 | Zanen et al. ........... | 128/203.15 |
| 6,062,212 A | * | 5/2000 | Davison et al. ........ | 128/200.16 |
| 6,068,198 A | | 5/2000 | Gupta | |
| 6,196,219 B1 | * | 3/2001 | Hess et al. ............. | 128/200.21 |
| D441,859 S | * | 5/2001 | Pera ......................... | D24/110 |

FOREIGN PATENT DOCUMENTS

| | | | |
|---|---|---|---|
| DE | 19953317 C1 | * | 5/1999 |
| DE | 1304131 A1 | * | 10/2001 |
| EP | 1 205 199 | | 5/2002 |
| GB | 2 240 494 | | 8/1991 |
| GB | 2 291 135 | | 7/1996 |
| WO | 97/29851 | | 8/1997 |
| WO | 00/47334 | | 8/2000 |

\* cited by examiner

*Primary Examiner*—Henry Bennett
*Assistant Examiner*—Nihir Patel
(74) *Attorney, Agent, or Firm*—Merchant & Gould P.C.

(57) ABSTRACT

The invention relates to an aerosol generator that comprises an oscillating membrane that is provided with openings. The aerosol generator is further characterized in that the liquid container is impinged upon with negative pressure by displacing a sealing element using a slidable sleeve and a rotary sleeve.

22 Claims, 4 Drawing Sheets

AEROSOL GENERATOR

Figure 1:
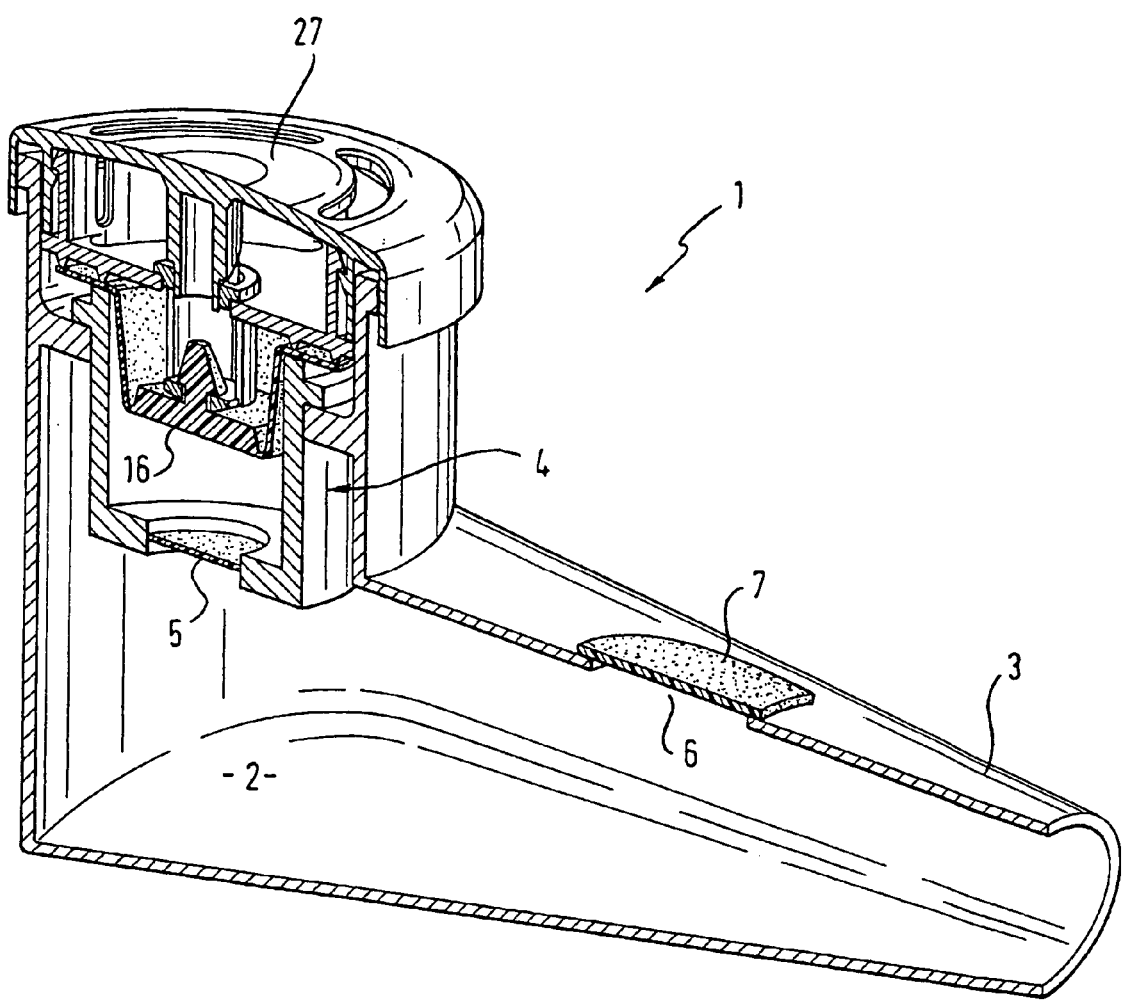

The invention relates to aerosol generators in which a liquid is nebulised by means of an oscillating membrane in particular for use in therapeutic aerosols.

Aerosol generators of this type comprise a liquid reservoir in which the liquid for the nebulisation is stored. The liquid is fed to a membrane that is brought to oscillation. The liquid present at one side of the oscillating membrane is hereby transported through openings in the oscillating membrane and takes the form of an aerosol on the other side of the oscillating membrane.

WO 97/29851, which describes an aerosol generator of this type, states that aerosol generators of this type work particularly effectively if the liquid feed takes place under a pressure slightly below the ambient pressure of the area into which the aerosol droplets generated by the membrane are emitted.

In order to assist the generation of the aerosol effectively and according to plan, the negative pressure must then in particular be generated within prespecified limits if the aerosol generator is to be used to nebulise a drug in a therapeutic aerosol. This is because the observance of specified parameters is decisive for the aerosol's droplet size and output rate and hence for the therapeutic application and efficacy since these values primarily determine the dose and deposition of the aerosol particles in the patient's lungs.

In addition, a therapeutic aerosol device with a membrane aerosol generator must as a whole be simple for the patient to operate as is also the case for the generation or establishment of the negative pressure in the liquid reservoir.

Against this background, the problem on which the invention is based is to identify an aerosol generator with a device for the generation of a negative pressure meeting the requirements described at the beginning.

Figure 2:
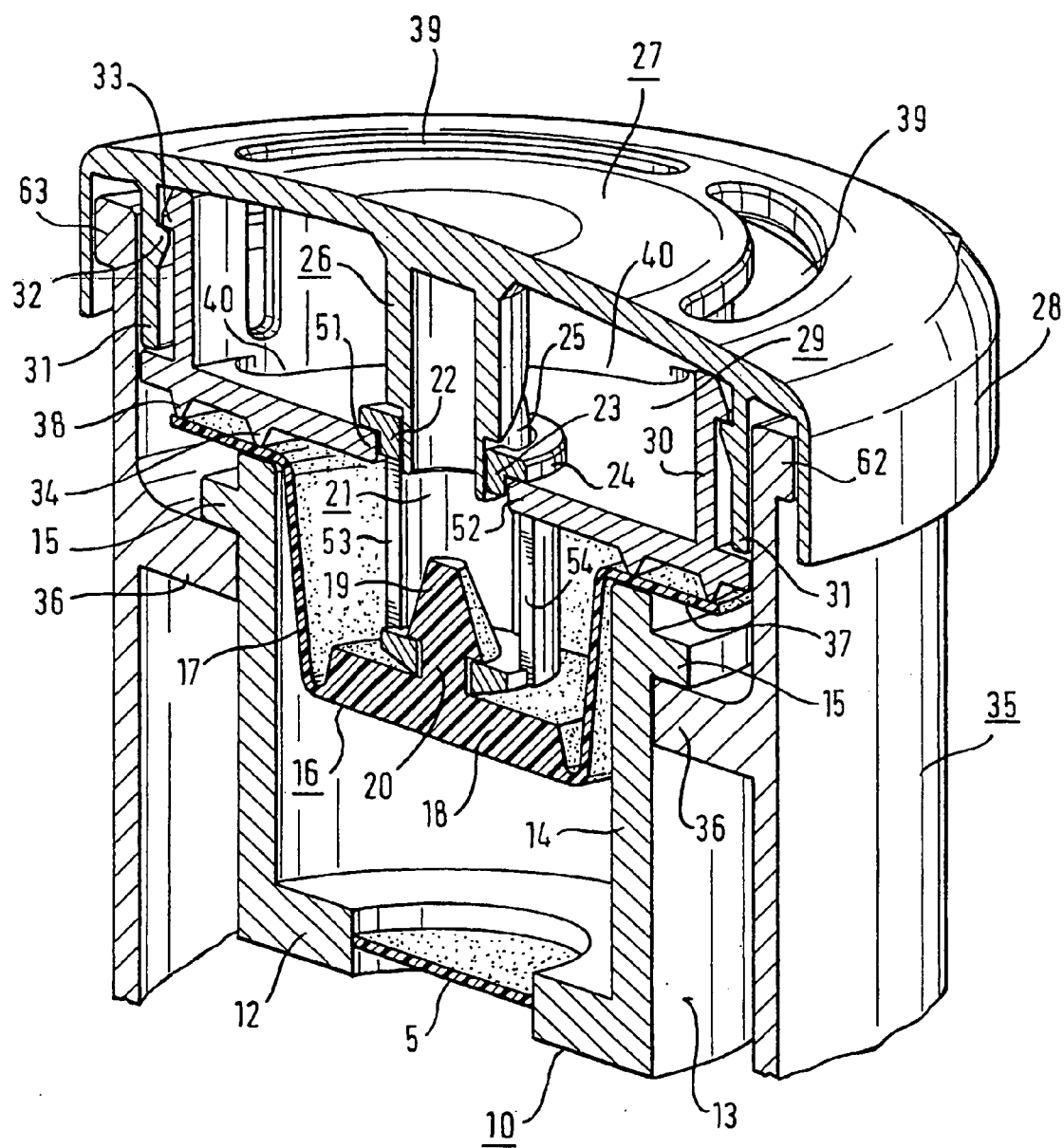
Figure 3:
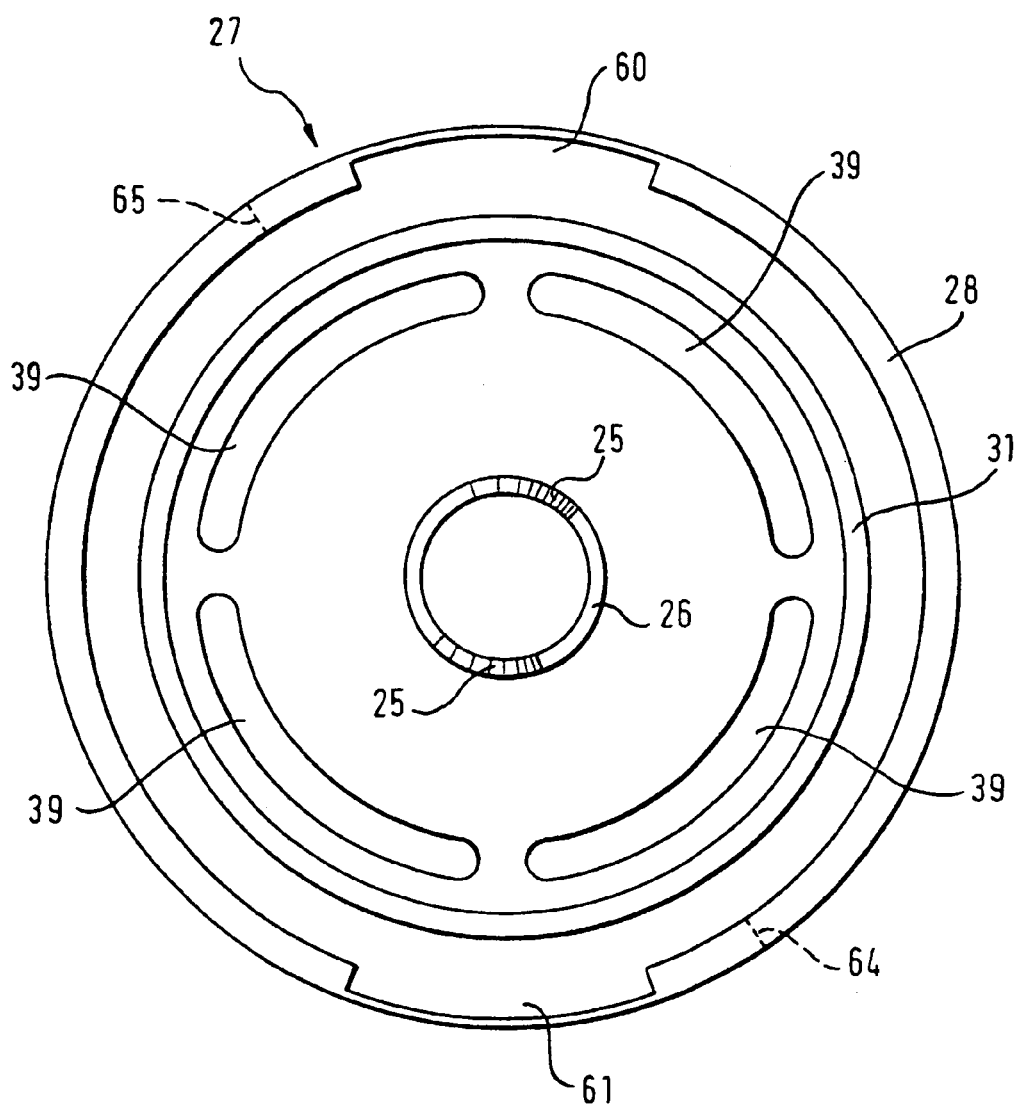
Figure 4:
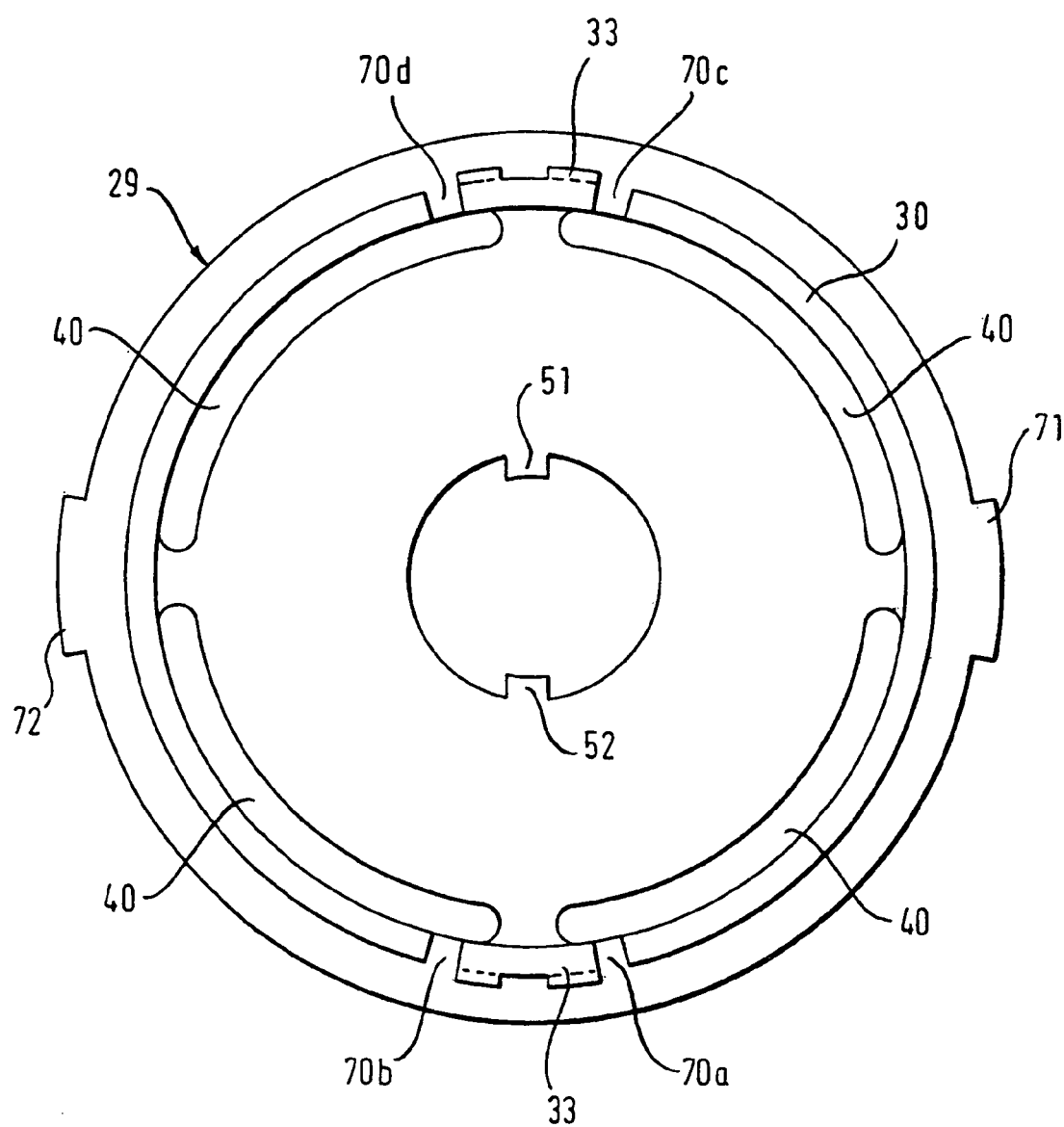

The invention will be further described with reference to an example of an embodiment shown in the drawings, which show:

FIG. 1 A therapeutic aerosol with an aerosol generator according to the invention FIG. 2 The aerosol generator according to the invention shown in FIG. 1 in an enlarged-representation FIG. 3 A top view of the handle of the aerosol generator according to the invention, and FIG. 4 A top view of the bearing sleeve in the aerosol generator according to the invention shown in FIG. 2.

FIG. 1 shows a therapeutic aerosol 1 with a nebulising chamber 2, a mouthpiece 3 and a membrane aerosol generator 4 whose oscillating membrane is marked 5 in FIG. 1. The oscillating membrane may, for example, be brought to oscillation by annular piezo elements (not shown), examples of which are described inter alia in WO 97/29851. When in use, the liquid is located on one side of the oscillating membrane 5, see top of FIG. 1, and this liquid is then transported through openings in the oscillating membrane 5 and emitted on the other side of the oscillating membrane 5, see bottom of FIG. 1, as an aerosol into the nebulising chamber 2. The patient is able to breathe in the aerosol present in the nebulising chamber 2 at the mouthpiece 3. So that the patient does not have to put down the therapeutic device after inhaling the aerosol, the mouthpiece 3 has an opening 6 sealed by an elastic valve element 7. If the patient exhales into the mouthpiece 3 and hence into the nebulising chamber 2, the elastic valve element 7 opens so that the exhaled air is able to escape from the interior of the therapeutic aerosol. On inhaling, ambient air flows through the aerosol generator 4 and this will be described in more detail below.

Firstly, however, there follows a description of the structure of the aerosol generator according to the invention with reference to FIG. 2.

The aerosol generator according to FIG. 2 described here as an example comprises a cylindrical storage vessel 10 to supply a liquid that is fed to the membrane 5. As shown in FIG. 2, the oscillating membrane 5 may be arranged in an end wall 12 of the cylindrical liquid reservoir 10 to ensure that the liquid poured into the liquid reservoir comes into direct contact with the membrane 5 when the aerosol generator according to the invention is held in the position shown in FIG. 1. However, other methods may also be used to feed the liquid to the oscillating membrane without any change being necessary to the design of the device according to the invention for the generation of a negative pressure in the liquid reservoir. However, due to the compact design of the aerosol generator according to FIGS. 1 and 2, this embodiment is particularly advantageous.

On the side facing the end wall 12, the cylindrical liquid container 10 is open. The opening is used to pour the liquid into the liquid reservoir 10. Slightly below the opening on the external surface 13 of the peripheral wall 14 there is a projection 15 which serves as a support when the liquid container is inserted in an appropriately embodied opening in a housing 35.

The open end of the liquid container 10 is closed by a flexible sealing element 16. The sealing element 16 lies on the end of the peripheral wall 14 of the liquid container 10 and extends in a pot-shaped way into the interior of the liquid container 10 whereby a conically running wall section 17 is formed in the sealing element 16 and closed off by a flat wall section 18 of the sealing element 16. As will be explained again below, forces act via the flat wall section 18 on the sealing element 16 and so the flat wall section 18 is preferably thicker than the other sections of the sealing element 16. On the perimeter of the flat wall section 18, there is a distance to the conical wall section 17 so that the conical wall section 17 may be folded when the flat wall section 18 is moved upwards, relative to the representation in FIG. 2.

On the side of the flat wall section 18 facing away from the interior of the liquid container, there is a projection comprising a truncated cone section 19 and a cylindrical section 20. This design enables the projection to be introduced and latched into an opening adapted to match the cylindrical section since the flexible material of the sealing element 16 permits the deformation of the truncated cone section 19.

According to the invention, the aerosol generator 4 comprises a slidable sleeve 21 equipped with an opening of this type which is substantially a hollow cylinder open on one side. The opening for the attachment of the sealing element 16 is embodied in an end wall of the slidable sleeve 21. When the truncated cone 19 has latched into place, the end wall of the slidable sleeve 21 containing the opening lies on the flat sealing element wall section 18. The latching of the truncated cone 19 into the slidable sleeve enables forces to be transmitted from the slidable sleeve 21 onto the flat wall section 18 of the sealing element 16 so that the sealing section 18 follows the movements of the slidable sleeve 21 in the direction of the central longitudinal axis of the liquid container 10.

In a generalised form, the slidable sleeve 21 may be seen as a slidable element, which may, for example, also be implemented as a slidable rod which may be stuck-on or inserted in a drill hole. Characteristic of the slidable element 21 is the fact that it may be used to apply a substantially linearly directed force onto the flat wall element 18 of the sealing element 16. Overall, the decisive factor for the mode of operation of the aerosol generator according to the invention is the fact that a slidable element transmits a linear movement onto the sealing element so that an increase in volume occurs within the liquid reservoir 10. Since the liquid reservoir 10 is otherwise gas-tight, this causes a negative pressure to be generated in the liquid reservoir 10.

The sealing element 16 and the slidable element 21 may be produced in one piece, i.e. in one operation, but from different materials. The production technology for this is available so that a one-piece handlable component for the aerosol generator according to the invention is created which may be produced in a fully automatic production step.

The slidable sleeve 21 is open on the end facing the drill hole for the truncated cone but at least two preferably diametrically opposite lugs 22 and 23 protrude radially into the interior of the slidable sleeve 21. A collar 24 encircling the slidable sleeve extends radially outwards. While the collar 24 is used as a support for the slidable sleeve 21 in the position shown in FIG. 2, the projections 22 and 23 protruding into the interior of the slidable sleeve 21 are used to absorb the forces acting on the slidable sleeve 21 in particular parallel to the central longitudinal axis. According to the invention, these forces are generated by means of two spiral grooves 25 which are located on the outside of the peripheral wall of a rotary sleeve 26.

The device according to the invention may also be implemented with one of the projections 22 or 23 and one groove 25. However, preference should be given to a uniformly distributed arrangement of two or more projections and a corresponding number of grooves.

The rotary sleeve 26 is also a cylinder open on one side whereby the open end is arranged in the slidable sleeve 21 and is hence facing the truncated cone 19 enabling the truncated cone 19 to penetrate the rotary sleeve 26. In addition, the rotary sleeve 26 is arranged in the slidable sleeve 21 is such a way that the projections 22 and 23 lie in the spiral grooves 25. The inclination of the spiral groove 25 is designed so that, when the rotary sleeve 26 is rotated in relation to the slidable sleeve 21, the projections 22 and 23 slide along the spiral grooves 25 causing a force directed parallel to the central longitudinal axis to be exerted on the sliding projections 22 and 23 and hence on the slidable sleeve 21. This force displaces the slidable sleeve 21 in the direction of the central longitudinal axis so that the sealing element 16 which is latched into the slidable sleeve's drill hole by means of the truncated cone is also substantially displaced parallel to the central longitudinal axis.

The displacement of the sealing element 16 in the direction of the central longitudinal axis of the liquid container 10 generates a negative pressure in the liquid container 10, determined inter alia by the distance by which the slidable sleeve 21 is displaced in the direction of the central longitudinal axis. The displacement causes the volume of the gas-tight liquid container 10 to increase and thereby a negative pressure to be generated. This displacement is in turn defined by the design of the spiral grooves 25 in the rotary sleeve 26. In this way, the aerosol generator according to the invention ensures that the negative pressure in the liquid reservoir 10 may be generated in the relevant areas by means of simple structural measures.

To ensure that the forces to be applied to generate the negative pressure when handling the device remain low, the rotary sleeve 26 is embodied in one piece with a handle 27 whose size is selected to enable the user to rotate the handle 27, and hence the rotary sleeve 26, manually without great effort. The handle 27 substantially has the shape of a flat cylinder or truncated cone which is open on one side so that a peripheral gripping area 28 is formed on the external periphery of the handle 27 which is touched by the user's hand to turn the handle 27. Due to the design of the spiral grooves 25 and the overall comparatively short distance to be travelled by the slidable sleeve 21 in the longitudinal direction to generate a sufficient negative pressure, it is only necessary to turn the handle 27 and hence the rotary sleeve 26 through a comparatively small angle. In preferred embodiments, this angle of rotation lies within a range from 45° to 360°. This embodiment makes a significant contribution to the ease of handling of the device according to the invention and an aerosol generator or therapeutic aerosol equipped therewith.

In order to create a unit which may be operated simply and uniformly from the slidable sleeve 21 and the rotary sleeve 26 including the handle 27, the example of an embodiment of the aerosol generator described here has a bearing sleeve 29 for bearing the slidable sleeve 21, which substantially comprises a flat cylinder open on one side. The diameter of the peripheral wall 30 of the bearing sleeve 29 is smaller than the internal diameter of the handle 27 and, in the example of an embodiment described, is aligned on the internal diameter of a cylindrical latching ring 31 which is provided concentrically to the gripping area 28 of the handle 27 but with a smaller diameter on the side of the handle 27 on which the rotary sleeve 26 is also arranged. Embodied on the side of the cylindrical latching ring 31 facing the rotary sleeve is a peripheral latching edge 32 which may be brought into engagement with latching lugs 33 situated at intervals on the peripheral wall 30 of the bearing sleeve 29. This enables the handle 27 to be located on the bearing sleeve 29 whereby, as shown in FIG. 2, the handle 27 is placed on the open end of the bearing sleeve 29 and the latching edge 32 is interlatched with the latching lugs 33.

To hold the slidable sleeve 21, an opening is provided in the centre of the sealed end of the bearing sleeve 29 in which the slidable sleeve 21 is arranged, as may be identified in FIG. 2. The collar 24 of the slidable sleeve 21 lies in the position shown in FIG. 2 on the surface of the end wall of the bearing sleeve 29 facing the handle. Extending into the bearing opening are two diametrically opposite projections 51 and 52, which protrude into two longitudinal grooves 53 and 54 on the peripheral surface of the slidable sleeve 21. The longitudinal grooves 53 and 54 run parallel to the longitudinal axis of the slidable sleeve 21. The guide projections 51 and 52 and the longitudinal grooves 53 and 54 provide anti-rotation locking for the slidable sleeve 21 so that the rotational movement of the rotary sleeve 26 results not in rotation but in the linear displacement of the slidable sleeve 21. As is evident from FIG. 2, this ensures that the slidable sleeve 21 is held in the combination of the handle 27 and the bearing sleeve 29 in an axially displaceable way but locked against rotation. If the handle 27 is now rotated in relation to the bearing sleeve 29, the rotary sleeve 26 also rotates in relation to the slidable sleeve 21 whereby the sliding projections 22 and 23 move along the spiral grooves 25. This causes the slidable sleeve 21 to be displaced in an axial direction in the opening of the bearing sleeve 29.

It is possible to dispense with the guide projections 51 and 52 in the bearing opening and the longitudinal grooves 53 and 54 in the slidable sleeve 21 if the design of the truncated cone 19 and the cylinder sections 20 of the sealing elements 16 and the large-area support for the slidable sleeve 21 holding the truncated cone on the flat sealing element section 18 achieves anti-rotation locking of the slidable sleeve 21 by means of friction. For this, the sealing element 16 has to be fixed so it is unable to rotate in relation to the bearing sleeve 29.

Provided on the surface of the sealed end of the bearing sleeve 19 facing away from the handle is an annular first sealing lip 34 concentric to the opening holding the slidable sleeve. The diameter of the first sealing lip 34 corresponds to the diameter of the peripheral wall 14 of the liquid container 10. As may be identified from FIG. 2, this ensures that the first sealing lip 34 presses the sealing element 16 on the end of the peripheral wall against the liquid reservoir 10 in such a way that the liquid reservoir 10 is sealed. In addition, the first sealing lip 34 may also fix the sealing element 16 so that it is unable to rotate in relation to the liquid reservoir 10 and the bearing sleeve 29. Due to the materials normally used for the sealing element on the one hand and the other components of the device according to the invention on the other, no excessive force needs to be applied in order to ensure that the aforesaid components of the device according to the invention are unable to rotate in relation to each other.

With the advantageous example of an embodiment described here, the forces required are generated at least to some extent by means of an interaction between the handle 27 and the housing 35 in which the liquid reservoir is embodied as one piece or in which the liquid reservoir 10 is inserted as shown in FIG. 2. In this case, the liquid reservoir 10 inserted in the casing with the peripheral projection 15 lies at intervals on a support 36 in the housing 35 which extends radially into the interior of the housing 35. This enables the liquid reservoir 10 to be easily removed from the housing 35 for purposes of cleaning. Since support is only provided at intervals, openings are provided for ambient air when the patient inhales, as is described in more detail below.

Partially identifiable only in FIG. 2 is the rotary lock, which is implemented by means of the handle 27 on the one hand and the housing 35 on the other. Only shown are the locking projections 62 and 63 on the housing 35. However, there are no special requirements with regard to the design of the rotary lock as far as the device according to invention is concerned for the generation of the negative pressure in the liquid reservoir 10.

With reference to FIG. 3, here a special embodiment of the rotary lock is described in which the handle 27 and the bearing sleeve 29 are matched to each other.

FIG. 3 shows a top view of the handle 27 from the side onto which the bearing sleeve 29 (not shown in FIG. 3) is plugged. As may be identified in the view in FIG. 3, the cylindrical part 28 of the handle 27 comprises recesses 60 and 61 in which the correspondingly embodied locking projections 62 and 63 of the housing (cf. FIG. 2) may be introduced. If the handle 27 is rotated, the projections 62 and 63 slide in grooves, not shown, in the bayonet lock as far as the stops 64 and 65; in FIG. 3, this corresponds to the rotation of the handle 27 shown in a counterclockwise direction. Also identifiable in FIG. 3, is the cylindrical latching ring 31 the latching edge 32 of which (cf. FIG. 2) is used to latch the handle 27 with the bearing sleeve 29. Arranged centrally and concentrically to the gripping area 28 and latching ring 31 is the rotary sleeve 26, which is embodied as one piece with the handle 27 and on which the spiral grooves 25 may be identified.

FIG. 4 shows the bearing sleeve 29, namely from the side faced by the handle 27 in latched-in position. The two diametrically arranged guide projections 51 and 52 protrude into the central opening, which holds the slidable sleeve 21. Also identifiable is the peripheral wall 30 which is interrupted at four points 70a, 70b, 70c and 70d to form the elastic latching lugs 33 which interact with the latching edge 32 on the latching ring 31 of the handle 27. The recesses 70a–70d mean the latching lugs 33 are springy so that interlatching may take place by drawing back the latching lug elements 33 when the bearing sleeve 29 is inserted in the handle 27. Vertically aligned in relation to the arrangement of the guide projections 51 and 52 are locking projections 71 and 72 provided diametrically on the external periphery of the beating sleeve which may be introduced into corresponding recesses in the housing 35 (not shown) of the therapeutic aerosol. The arrangement of the guide projections 51 and 52, the locking projections 71 and 72 and the spiral grooves 25 (cf. FIG. 3) achieves a basic setting assumed by the handle 27 in relation to the bearing sleeve 29 when the two elements are interlatched. Following this, the handle 27 is plugged onto the housing 35 as a sort of lid so that the projections 62 and 63 of the housing 35 are introduced into the bayonet openings 60 and 61 and simultaneously the locking projections 71 and 72 into the recesses in the housing 35. The recesses in the housing 35 and the locking projections 71 and 72 in the bearing sleeve 29 and the projections 62 and 63 of the housing 35 for the bayonet openings 60 and 61 are ranged at right angles to each other. This means that alter placing the handle on the housing, the patient may interlock the bayonet lock in one operation and effect a movement of the rotary and slidable sleeves giving rise to the negative pressure and the sealing of the liquid container.

With the example of the embodiment shown here, the sealing element 16 is advantageously embodied in such a way that, in addition to the functions mentioned above, the same sealing element functions as an exhalation valve. For this, the sealing element 16 on the section arranged on the end of the peripheral wall 14 of the liquid reservoir 10 is fitted with a valve section 37, which continues the sealing element 16 in one piece and extends radially beyond the peripheral wall 14 of the liquid reservoir 10. The bearing sleeve 29 comprises a second sealing lip 38 which runs concentrically to the first sealing lip 34 and has a diameter greater than tat of the first sealing lip 34. Due to the fixation of the sealing element 16 by means of the first sealing lip 34 and the peripheral wall 14 of the liquid reservoir 10, a second section is defined as the valve section 37 which implements a non-return valve in conjunction with the second sealing lip. To facilitate air flow, openings 39 and 40 are provided in the handle 27 and the end wall of the bearing sleeve 29 through which the ambient air is able to flow (cf. also FIGS. 3 and 4). The extended section 37 of the sealing element 16 is then deflected from the neutral position in which the extended section 37 lies on the second sealing lip 38.

Particularly advantageous with this embodiment is the circumstance that the sealing element 16 is embodied in one piece and takes over both the function of the piston 16 and 18 for the generation of the negative pressure in the liquid reservoir 10 and the function of the flexible valve element 37 for the exhalation non-return valve. Since the sealing element 16 is attached to the slidable sleeve 21 and the latter is in turn fastened to the bearing sleeve 29, the device according to the invention is endowed with a uniformly handlable component group which also includes the non-return valve.

As may be seen in FIGS. 3 and 4 in conjunction with FIG. 1, a user of the device according to the invention is able to put on the therapeutic aerosol device's lid formed by the handle with one grip and by rotating around the central longitudinal axis achieve both an interlocking of the lid and the displacement of the slidable sleeve and hence the generation of the negative pressure in the liquid container. The user simultaneously attaches the exhalation non-return valve to the therapeutic aerosol device and seals the liquid container.

What is claimed is:

1. Aerosol generator in particular for therapeutic aerosols with
   an oscillating membrane to one side of which a liquid may be fed and which may be brought to oscillation in order to transport the liquid through openings in the oscillating membrane and to emit the liquid in the form of an aerosol on the other side of the oscillating membrane,
   a liquid reservoir to hold the liquid connected to the oscillating membrane to feed the liquid, wherein the membrane constitutes a wall portion of the liquid reservoir,
   a sealing element arranged on an opening in the liquid reservoir to provide a gas-tight seal for the opening, and
   a slidable element connected to the sealing element in such a way that a movement of the slidable element effects a movement of at least one section of the sealing element whereby a negative pressure is generated in the liquid reservoir so that the liquid presently fed to the membrane is under negative pressure.

2. Aerosol generator according to claim 1, wherein a rotary element is provided which is connected to the slidable element in such a way that the rotation of the rotary element around the longitudinal axis effects a substantially linear movement of the slidable element.

3. Aerosol generator according to claim 1, wherein the slidable element is a slidable sleeve and the rotary element is a rotary sleeve.

4. Aerosol generator according to claim 1, wherein the sealing element comprises an elastic material so that the sealing element is deformable at least in some areas.

5. Aerosol generator according to claim 1, wherein the slidable element and the sealing element are produced in one piece from different materials.

6. Aerosol generator according to claim 1, wherein the sealing element has a flat section on which there is a projection and that the slidable element has an opening in which the projection is arranged to connect the slidable element with the sealing element.

7. Aerosol generator according to claim 6, wherein the projection comprises a truncated cone section and a cylindrical section and the opening in the slidable sleeve is adapted to match the cylindrical section.

8. Aerosol generator according to claim 1, wherein the sealing element has a conical wall section which is sealed off from the flat wall section.

9. Aerosol generator according to claim 8, wherein between the flat wall section and the conical wall section there is a area surrounding the flat wan section embodied in such a way that the flat wall section is separated from the conical wall section.

10. Aerosol generator according to claim 3, wherein the slidable sleeve is a first cylinder open on one side comprising at least two sliding projections on the open end extending radially into the interior of the cylinder and that the rotary sleeve is a second cylinder open on one side comprising on the external peripheral surface at least two spiral grooves and arranged in the slidable sleeve in such a way that the sliding projections are each arranged in a spiral groove.

11. Aerosol generator according to claim 10, wherein the slidable sleeve is embodied in one piece wit a handle facilitating the manual rotation of the rotary sleeve.

12. Aerosol generator according to claim 11, wherein the handle is substantially a flat cylinder or truncated cone with a gripping area.

13. Aerosol generator according to claim 11, wherein the handle comprises a latching ring with a latching edge and a bearing sleeve is provided comprising latching lugs for interlatching the bearing sleeve and the latching edge of the handle and in which there is an opening in which the slidable sleeve is arranged.

14. Aerosol generator according to claim 13, wherein the slidable sleeve comprises a peripheral edge lying on the bearing sleeve in at least one position.

15. Aerosol generator according to claim 13, wherein the bearing sleeve comprises a first sealing lip for pressing the sealing element onto a surface of the liquid reservoir surrounding the opening in the liquid reservoir sealed by the sealing element.

16. Aerosol generator according to claim 15, wherein the bearing sleeve comprises a second sealing lip arranged concentrically to the first sealing lip and that the sealing element comprises a valve section for the realization of a inhalation valve extending between the first and second sealing lips.

17. Aerosol generator according to claim 3, wherein the bearing sleeve in the peripheral surface comprises at least one longitudinal groove interacting with at least one guide projection for the anti-rotation locking of the bearing sleeve.

18. Aerosol generator according to claim 17, wherein the guide projection is arranged in the opening of the bearing sleeve.

19. Aerosol generator according to claim 1, wherein the oscillating membrane is arranged in one end of the liquid reservoir.

20. Therapeutic aerosol with an aerosol generator according claim 1.

21. Therapeutic aerosol according to claim 20, wherein the handle of the therapeutic aerosol is embodied as a lid and may be connected to the housing of the therapeutic aerosol by means of a rotary lock.

22. Therapeutic aerosol to according to claim 20, wherein the bearing sleeve comprises at least one projection interacting with a latching groove in the housing of the therapeutic aerosol for the anti-rotation locking of the bearing sleeve.

* * * * *